United States Patent [19]

Swanson

[11] 4,205,550
[45] Jun. 3, 1980

[54] SAMPLE CHAMBER FOR GAS ANALYZER

[75] Inventor: S. Keith Swanson, Saratoga, Calif.

[73] Assignee: Econics Corporation, Cupertino, Calif.

[21] Appl. No.: 19,891

[22] Filed: Mar. 12, 1979

[51] Int. Cl.² ............................................ G01N 21/26
[52] U.S. Cl. ............................... 73/1 G; 73/421.5 A; 356/438
[58] Field of Search ......................... 73/1 G, 421.5 A; 356/437, 438, 439, 440; 250/576; 350/63

[56] References Cited

U.S. PATENT DOCUMENTS

| 1,969,626 | 8/1934 | Simon | 356/438 |
| 3,847,487 | 11/1974 | Boll | 356/438 |

FOREIGN PATENT DOCUMENTS 1039955  8/1966  United Kingdom ...................... 350/63

OTHER PUBLICATIONS

Webb et al., True On-Line and Span Determination for Continuous Emission Monitoring System.

Primary Examiner—S. Clement Swisher
Attorney, Agent, or Firm—Limbach, Limbach & Sutton

[57] ABSTRACT

In a duct having a gas of predetermined density and viscosity flowing therethrough at a predetermined velocity, a sample chamber for a gas analyzer for use in such a duct is disclosed and includes an inner chamber having a passage therethrough and an outer chamber at least partially surrounding the inner chamber and having a pair of apertures, with the outer housing being movable by suitable apparatus between one position in which the outer housing apertures are generally aligned with the inner chamber passage and another position in which the outer housing apertures are spaced from the inner chamber passage, the outer housing and inner chamber being configured and dimensioned such that the Reynolds number for the flow of duct gases over the outer housing and inner chamber is sub-critical when the outer housing is in its other position with its apertures spaced from the inner chamber passage.

15 Claims, 7 Drawing Figures

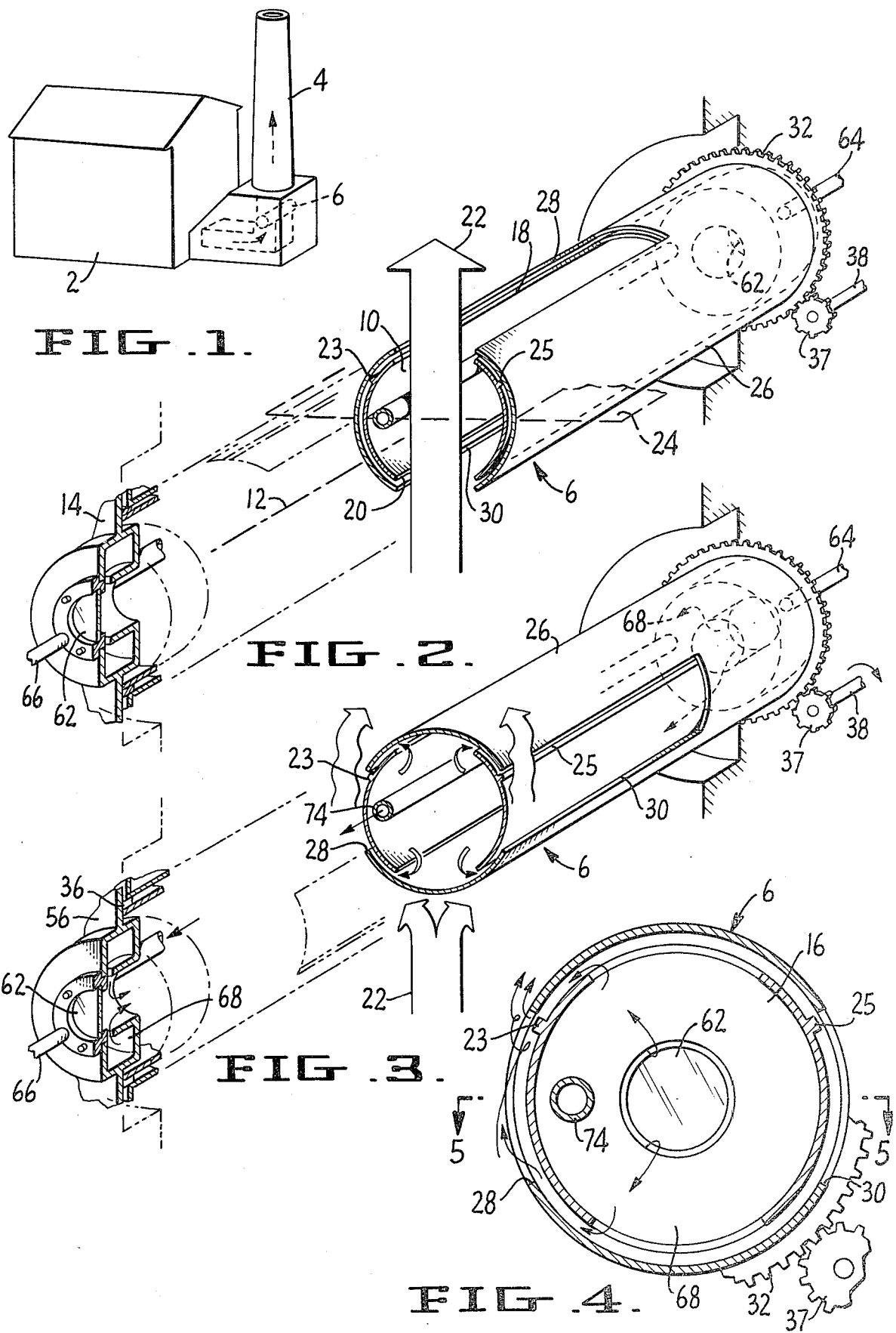

SAMPLE CHAMBER FOR GAS ANALYZER

BACKGROUND OF THE INVENTION

Duct gas analyzers which are mounted in ducts or flues typically include a source unit containing a source of suitable radiation, such as infrared, ultraviolet and visible light, mounted on one side of the duct or flue. A detector unit containing sensing devices for separating and measuring the specific wave lengths for analysis of the duct gases is mounted on the opposite side of the duct or flue. The source unit and the detector unit are typically connected by some member, such as a pipe, which serves both as an alignment fixture and as a sample cell, with apertures in the pipe allowing the duct gases to flow through the sample cell, which extends across the path of flow of the gases.

Windows of various types are typically used to isolate the source and detector units from the duct gases to protect the source, detectors and their associated electronic components. Additionally, fresh air is normally brought into the sample chamber and passed over the window faces to provide some cleansing action and to maintain a clean air region between the duct gases and the window. While this fresh air helps to keep the windows clean, over an extended time period deposits from the duct gases, particularly when these gases are gases of combustion from a furnace, build up on the window and cause errors in the qualitative and quantitative determination of the duct gas constituents. One method of correcting for this problem, caused by the deposit build-up is to block the apertures through which the duct gases enter and leave the sample cell to allow the fresh air introduced from outside to clean or purge the cell of the duct gases. During this purging the signal from the detectors may be measured to provide an indication of the error signal being caused by the deposit coating on the windows.

In one type of prior art apparatus the sample cell is in the form of a pipe having apertures aligned with the gas flow and having a pair of doors hingedly mounted to the sample cell to close off those apertures when swung to their closed position against the cell and to open those apertures when swung back away from the cell. This prior art apparatus, while providing advantages over those sample cells having no means for closing the apertures, possesses a number of disadvantages itself. For example, the doors require a relatively tight seal to achieve effective purging, a seal which is difficult to achieve and maintain over time, particularly when exposed to high temperature combustion gases. Additionally, in applications where there are large quantities of particulate matter in the duct gases, a build-up of the deposits around the door openings can prevent the doors from closing to exclude the duct gases from the chamber for purging. Such an apparatus also requires, in large scale applications, high powered fans to provide sufficient fresh air to clear the chambers. Additionally, where such sample chambers are mounted through an aperture in the duct wall, which aperture is only slightly larger than the cross-section of the closed sample chamber, a malfunction of the door closing apparatus may create sufficient mechanical interference to preclude removal of the sample chamber for service without shutting down the furnace, boiler, or other apparatus connected with the duct.

In fluid mechanics there are well known techniques for determining the pressure distribution of a flowing stream of gases at various points over a body immersed in that stream. However, none of the prior art known to the applicant has taken advantage of the kinetic energy in such a stream to assist in the operation, and particularly the purging, of a gas analyzer sample chamber.

OBJECTS OF THE INVENTION

In view of the disadvantages of the prior art sample chamber apparatus, it is an object of this invention to provide an improved sample chamber for a duct gas analyzer which will provide for compensation of deposit build-ups within the sample chamber.

It is a further object of this invention to provide such apparatus which can be inserted into or removed from a duct through a relatively small aperture in the duct regardless of whether the chamber is in an open or closed condition.

It is yet another object of the invention to provide such a sample chamber in which tight seals are not required to achieve effective purging, and which makes use of the kinetic energy of the flowing gas stream to assist in the purging.

Briefly, this invention relates to a sample chamber for a gas analyzer for use in a duct containing the gases to be analyzed, which gases have a predetermined density, viscosity, and flow velocity, this sample chamber including an elongated inner chamber, and an outer housing which at least partially surrounds the inner chamber. The inner chamber has a longitudinal axis and a passage through the inner chamber, which passage is generally transverse to the axis and is defined by at least a pair of apertures through the longitudinally extending sides of the inner chamber and on opposite sides of a plane which includes the axis. The outer housing also has a longitudinal axis which is generally parallel to the inner chamber axis, and the outer housing includes at least a pair of apertures therethrough on opposite sides of a plane which includes the outer housing axis. This outer housing is movable between one position in which the outer housing apertures are generally aligned with the inner chamber apertures, and another position in which the outer housing apertures are spaced from the inner chamber apertures. In the one position the inner chamber apertures are open for passage of gases through the inner chamber and in the other position the inner chamber apertures are covered by the outer housing to restrict the flow of gases through the inner chamber. The inner chamber and outer housing are configured and dimensioned such that the Reynolds number for the flow of gases over the outer housing and inner chamber is sub-critical when the outer housing is in such other position. Suitable apparatus is provided for moving the outer housing between the one position and the other position.

BRIEF DESCRIPTION OF THE DRAWINGS

A particularly preferred embodiment of the apparatus of this invention will be described in detail below in which:

FIG. 1 is a schematic view, in perspective, of a typical application of the gas sample chamber of this invention;

FIG. 2 is a fragmentary perspective view of a preferred embodiment of the sample chamber of this invention in an open configuration such that duct gases may freely flow through the chamber;

FIG. 3 is a perspective view of the apparatus of FIG. 2 in its closed configuration for purging;

FIG. 4 is a sectional view of the apparatus of FIG. 3 looking toward the right hand end thereof;

DESCRIPTION OF A PREFERRED EMBODIMENT

In FIG. 1 a typical application of the gas sample chamber of this invention is illustrated schematically. While such a sample chamber may suitably be used in any duct for analyzing the gases flowing through that duct, it is illustrated here for use in conjunction with apparatus such as a furnace, which is not shown but is enclosed within building 2 and from which emanate combustion gases for discharge through the flue or smokestack 4. The sample chamber 6 is shown in phantom, grossly exaggerated in size for purposes of clarity of illustration, located in the flue 4. Thus it may be readily seen that the gases of combustion from the furnace flowing through the duct and flue 4 will also pass over the sample chamber 6, and a portion of these gases may be directed through the sample chamber for analysis when desired. The flow of the combustion gases over the sample chamber, which projects across the duct or flue, follows the principles of fluid mechanics.

Figure 6:
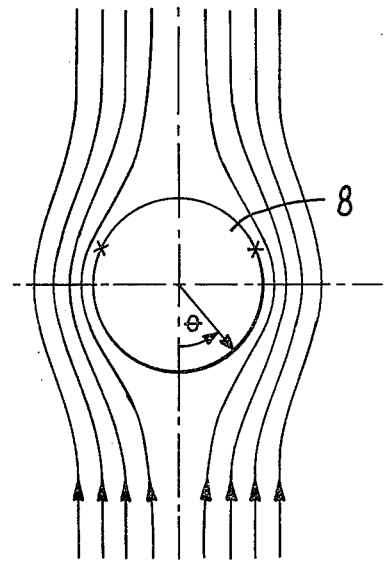
FIG. 6 is a schematic representation of frictionless flow about a circular cylinder.
Figure 7:
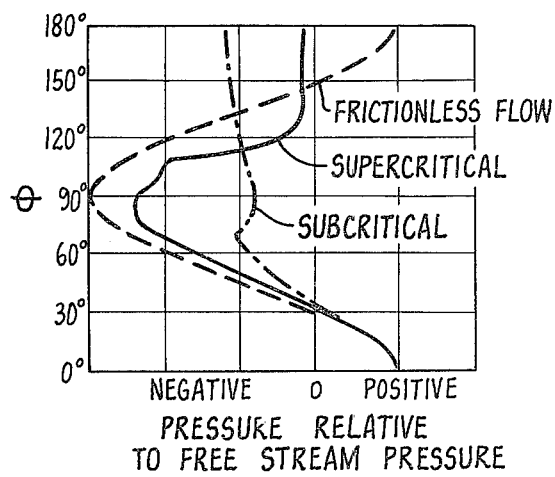
FIG. 7 is a graphical representation of pressure distributions relative to free stream pressure around the circular cylinder of FIG. 6 extending normal to a stream of flowing fluid.

As is well known in fluid mechanics, the effects of a fluid flow, such as a gas or liquid flow, on different bodies immersed in a moving fluid stream may be predicted through the use of a dimensionless coefficient known as the Reynolds number. The Reynolds number incorporates the fluid's velocity, density, viscosity, and a characteristic diameter of the body immersed in the fluid stream under study. It is also well known that at low fluid velocities the pressure-velocity relationship for a cylinder immersed in a moving fluid flow follows Bernoulli's equation for total energy in the stream. However, at higher Reynolds numbers, the pressure relationship becomes more complex because of friction effects. This relationship is shown in FIG. 7, which graphically illustrates the pressure distribution around half of the cylinder 8 shown in section in FIG. 6 immersed in a fluid flow. As shown in the plot of FIG. 7 of pressure relative to free stream pressure at various angles $\theta$ about the axis of cylinder 8, the pressure is positive for angles less than about 30° and greater than about 150°. These relationships apply equally to the mirror image other half of the cylinder for angles taken from the upstream center of the cylinder around to the downstream side. These relationships and plots can be found in more detail in texts such as Flachsbart, *Reports of the Aerodynamic Versuchanstalt,* Geottingen, 4th Series, p. 134 (1932).

As the velocity and Reynolds number increase beyond the value for laminar flow, the retarding effect of fluid near the surface prevents the flow from following smoothly all the way around the body. As a result, separation of the flow from the surface occurs before the rear stagnation point (the downstream center of the cylinder in FIG. 6) is reached. The wake thus formed dissipates the kinetic energy of the fluid leaving the surface. This causes the drag coefficient to remain relatively constant over a wide range of Reynolds numbers until a critical point is reached, at which a sudden decrease occurs. At this point the greater kinetic energy of the fluid flowing around the sides of the cylinder causes the separation point to move rearward, increasing the pressures on the rear half. Subcritical Reynolds numbers are those whose values are between those for laminar flow and the critical point, i.e. between about 10,000 and 200,000 for flow around a cylinder. See Geidt, *Principles of Engineering Heat Transfer,* Van Nostrand, 1957. Thus, the pressure distribution of sub-critical and super-critical Reynolds number flows have distinct differences, as shown in FIG. 7. The preferred embodiment of the sample chamber of this invention takes advantage of these flow characteristics as described below.

Figure 5:
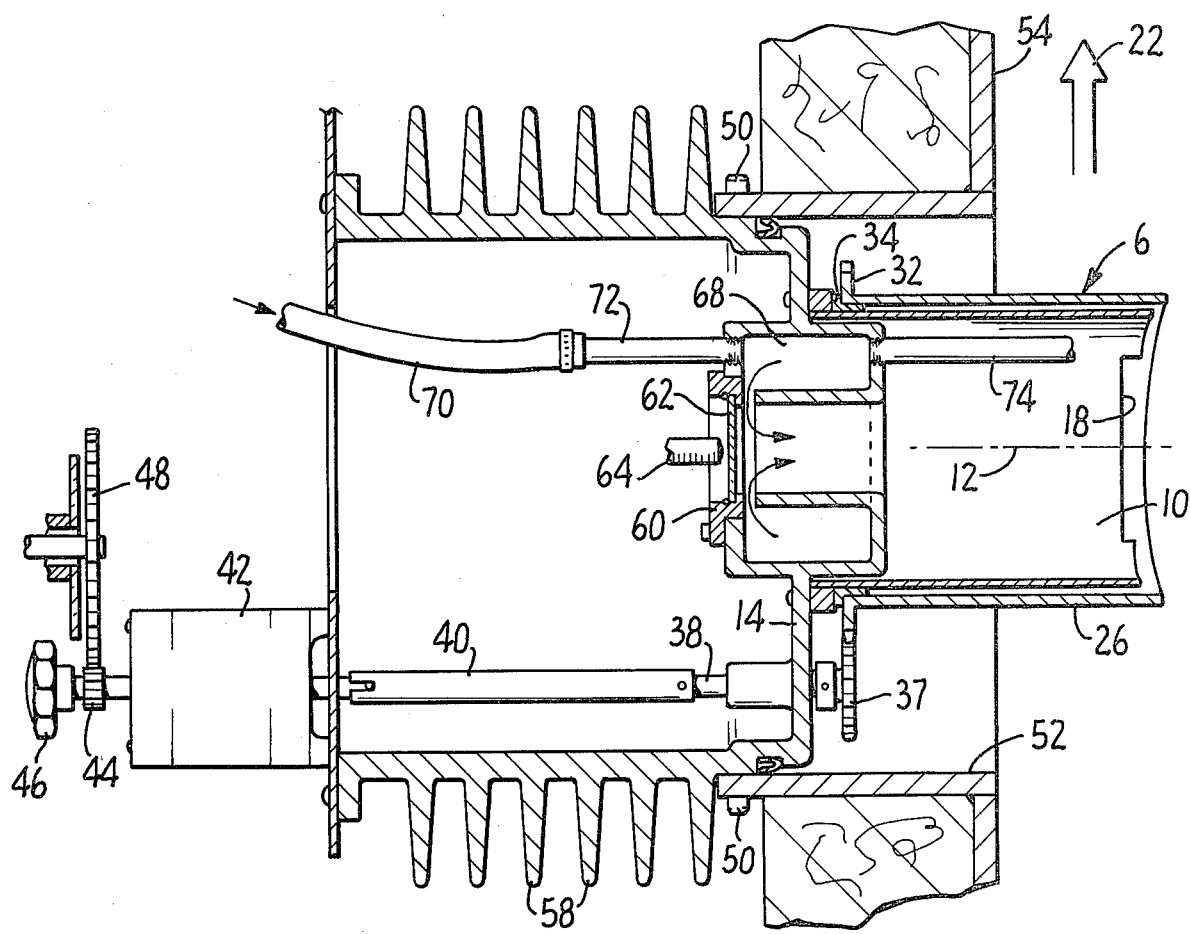
FIG. 5 is a plane view in section, taken through the center of the right hand end of the apparatus of FIG. 2.

As shown in FIG. 2, the sample chamber 6 of this preferred embodiment includes an elongated inner chamber 10, which suitably may be fabricated from a length of cylindrical tubing, such as aluminum or steel tubing, rigidly affixed at one end to end plate 14, shown in FIGS. 2, 3 and 5 and at the other end to end plate 16, shown in the sectional view of FIG. 4. A passage is provided through this inner chamber generally transverse to the longitudinal axis 12, with such passage being defined by the walls of the inner chamber and apertures 18 and 20, which are formed through the longitudinally extending sides of the inner chamber. The passage formed by these apertures is shown permitting the flow of duct gases, represented by the arrow 22, to pass through the inner chamber in the configuration of FIG. 2. As may be seen in FIG. 2, the apertures 18 and 20 are on opposite sides of an imaginary plane 24 which includes longitudinal axis 12 and is generally transverse to the direction of flow of gases indicated by arrow 22. These apertures 18 and 20 desirably subtend arcs about the axis 12 of less than 90°.

As shown in FIGS. 2 and 3 and more clearly in FIG. 4, a pair of extended tabs or ribs 23 and 25 affixed to or forming a part of the radially outer surface of the inner chamber 10 extend along that surface for substantially the entire longitudinal extent of the apertures in the outer housing described below. Suitably, these ribs or tabs 23 and 25 may extend the entire length of the inner chamber 10. As seen in FIG. 2 these extended tabs 23 and 25 are both positioned on the outer surface of the inner chamber 10 at points spaced from and on the same side of the previously described imaginary plane 24. The purpose of these extended tabs 23 and 25 will be explained more fully below.

Generally concentric with and at least partially surrounding the inner chamber 10 is an outer housing 26. This outer housing 26 may be of numerous suitable configurations, but in this embodiment is desirably formed of a length of cylindrical tubing, such as aluminum or steel tubing, having an inside diameter larger than the outside diameter of the inner chamber 20. While other housing configurations having a longitudinal axis only parallel to axis 12 are equally suitable, in this preferred embodiment the outer housing 26 is concentric with the inner chamber 10, also having axis 12 as its longitudinal axis. A pair of apertures 28 and 30 are provided through the longitudinal sides of outer housing 26, these apertures corresponding, as shown in FIG. 2, to the apertures 18 and 20 of the inner chamber 10, similarly being on opposite sides of the imaginary plane 24 which includes the axis 12.

The tubular portion of the outer housing 26 is attached at one end to a ring gear 32 which is supported by a low friction bushing 34 of nylon or other low friction material, which itself is supported by inner chamber 10. The opposite end of the tubular portion of outer housing 26 is supported by a similar bushing 36 which, in turn, is supported by the adjacent end of inner chamber 10. By means of these bushings 34 and 36 the outer housing 26 is supported for rotational movement about the longitudinal axis 12. This outer housing 26 may be driven for such rotational movement by ring gear 32, which is engaged by pinion 7 mounted to a shaft 38 which is journaled in end plate 14 and which in turn is connected to extension shaft 40, shown best in FIG. 5. This extension shaft 40 is connected, through a suitable separable joint, to an electric drive motor 42, which provides rotational force to the shafts and the pinion 7. At the end of motor 42 opposite the shaft connecting with extension shaft 40 may be provided another extension of the motor shaft having both a pinion 44 and a knob 46 affixed to it. The knob 46 provides for manual rotation of the pinion 7 when desired. The pinion 44 drives gear 48 which may be connected to a conventional shaft position indicator to show the rotational position of outer housing 26.

As best shown in FIG. 5, which is a sectional plan view of the end of the chamber having the drive motor and ring gear arrangement, the end plate 14 to which the various components are mounted, may be in the form of a somewhat complex cup-like structure which may be cast of a suitable material such as meehanite. This end plate structure 14 is mounted by suitable means, such as cap screws 50, to an inset ring 52 or other suitable structure forming part of the duct or flue carrying the gases to be analyzed. At the opposite end of the sample chamber 6 a smaller end plate structure 16 may be provided which is substantially similar to the portion of end plate 14 from a point immediately inward of the cooling fins 58. Thus, the sample chamber 6 of this preferred embodiment extends inwardly of the flue from one side thereof all the way across to the other side and through that other side, although another embodiment could extend from only one side of the duct.

At the radial center of each of the end plate structures 14 and 16 is provided a removably mounted window including a bezel 60 and a window 62 which is transparent to the radiation of interest. Adjacent the window 62, which suitably is normal to axis 12 and outside the sample chamber at one end, is provided a suitable and conventional source for the desired radiation, with a conventional detector 66 for that type of radiation being correspondingly positioned outside the window at the opposite end of the chamber. Alternatively, both the radiation source 64 and the detector 66 could be positioned side-by-side at one end of the chamber with the window 62 at the opposite end of the chamber being replaced with a reflective element, such as the mirror, so that the radiation from the source traverses the longitudinal extent of the chamber twice, from the source to the reflective element and from the reflective element back to the detector.

Adjacent the window structure at each end of the chamber an air plenum 68, generally concentric with the window 62 is provided as a portion of each end plate 14 and 16. At the end of this apparatus containing the drive motor 42 a source of pressurized air (not shown) is connected through tube 70 and pipe 72 to the plenum 68. From that plenum another pipe 74 conveys a portion of that pressurized air to the plenum 68 at the opposite end of the chamber. Both of these plenum chambers 68 provide the clean air which is used to purge the chamber of unwanted gases from the duct or flue in a manner to be described below.

In view of the structure of the preferred embodiment of the sample chamber of this invention described above, the manner of operation of this apparatus may now be seen, with particular respect to FIGS. 2, 3 and 4. As shown in FIGS. 2 and 3, the outer housing 26 is supported on the bushings 34 and 36 at its opposite axial ends, is movable, in this embodiment by means of rotation about axis 12, between one position in which its apertures 28 and 30 are generally aligned with the inner chamber apertures 18 and 20 (FIG. 2) and another position in which the outer housing apertures 28 and 30 are spaced from the inner chamber apertures 18 and 20 (FIG. 3). In the one position, shown in FIG. 2, the gases indicated by the arrow 22 may pass freely through the generally aligned apertures and thus through the inner chamber. When the outer housing 26 is moved, by rotation in the preferred embodiment to the other position of FIG. 3, with its apertures 28 and 30 generally facing transversely of the direction of flow of the gases in the flue or duct, the inner chamber apertures 18 and 20 are covered by the outer housing and deflect the flue gases (indicated by arrow 22) around the sample chamber apparatus.

In its preferred embodiment, the size, including diameter, and configuration of the inner chamber 10 and outer housing 26 of the sample chamber are selected with respect to the size of the duct and the rate of flow and density and viscosity of gases therethrough such that the Reynolds number for that flow and this apparatus remains in the sub-critical region at all times when the outer housing is in its other position closing off the inner chamber passages, shown on the qualitative plot of FIG. 7. For example, for a gas having a density of 0.075 lb/ft$^3$, a viscosity of 0.35 × 10$^6$ lb-sec/ft$^2$ and flowing at 50 ft/sec, the sample chamber diameter might suitably be about 6.5 inches. Thus, from FIG. 7 it may be seen that pressure of the stream on the outer surface of the chamber remains negative for all points around the chamber behind about 35° from the stagnation point facing dead ahead into the stream of duct gases. Thus, where the upstream edges of the apertures 28 and 30 lie more than about 35° behind that stagnation point, such as about 45° or more for the preferred embodiment as shown in FIG. 4, the pressure exerted by the gas stream as it flows by those apertures is less than the free stream pressure. Consequently, the flowing gases tend not to attempt to enter the chamber through the apertures 28 and 30 when they are positioned as shown in FIGS. 3 and 4, but rather tend to evacuate the interior of the sample chamber due to the pressure differential at those points with respect to the free stream pressure. Such evacuation, along with the fresh air introduced through the plenum chambers 68 serves to purge any of the duct gases from the sample chamber when the outer housing 26 is moved to the position illustrated in FIGS. 3 and 4.

Tabs 23 and 25, described above, can be seen in FIGS. 3 and 4 to be positioned on the inner housing 10 such that, when the outer housing 26 is in its purging position (FIGS. 3 and 4) these tabs 23 and 25 are just upstream from the downstream edge of the apertures 28 and 30. Thus, these tabs serve to create additional turbulence in the portion of the gas stream flowing over the sample chamber and which may bear against the portion of the outer surface of the inner chamber which is exposed to the outer housing apertures. Thus, any such duct gases are deflected away from the downstream edge of the outer housing apertures 28 and 30 and create an additional low-pressure area there to effect purging of the gases from the interior of the chamber and to block any migrant flow of duct gases into the sample chamber, as indicated by the various arrows in FIGS. 3 and 4. By virtue of these pressure differentials, it may be seen that the spacing of the radially outer portion of the inner chamber 10 from the radially inner portion of the outer housing 26 facilitates the purging of the interior of the sample chamber through the inner chamber apertures 18 and 20 and thence out the outer housing apertures 28 and 30. This arrangement eliminates the need for any tight seals which might degrade or be otherwise compromised by particulate matter in the stream of duct gases. Thus, any build-ups of deposits of such particulate matter will not prevent this sample chamber from functioning in the desired manner. Additionally, this concentric cylinder configuration eliminates problems of mechanical interference when inserting or removing the chamber through the side of the duct. As another additional consideration, this structure utilizes the kinetic energy of the flue gases to assist in the purging, thus avoiding the need for powerful blowers supplying high-pressure air to the plenum chambers 68.

The foregoing detailed description relates to a particularly preferred embodiment of the sample chamber of this invention and its operation and is intended to be only illustrative of the principles of this invention. Obviously, numerous variations and modifications of this apparatus, all encompassed within the scope of the invention, will readily occur to those skilled in the art. Such variations may include, among others, configurations of the inner chamber and outer housing other than the concentric cylinders described, and other means and methods of moving the outer housing between its open position and its purging position. In view of these and numerous other such variations and modifications, the scope of this invention is to be limited solely by the claims appended hereto.

I claim:

1. In a duct having a gas of predetermined density and viscosity flowing therethrough at a predetermined velocity a sample chamber for a gas analyzer for use in such duct, comprising elongated inner chamber means having a longitudinal axis and a passage through said inner chamber, which passage is generally transverse to said axis and is defined by at least a pair of apertures through the longitudinally extending sides of said inner chamber means and on opposite sides of a plane which includes said axis;

outer housing means at least partially surrounding said inner chamber means and having a longitudinal axis generally parallel to said inner chamber axis, said outer housing means having at least a pair of apertures therethrough on opposite sides of a plane which includes said outer housing axis, said outer housing means being movable between one position in which said outer housing apertures are generally aligned with said inner chamber apertures and another position in which said outer housing apertures are spaced from said inner chamber apertures, whereby in the one position the inner chamber apertures are open for passage of gases freely through the inner chamber passage and in the other position the inner chamber apertures are covered by the outer housing means to restrict flow of gases through the inner chamber passage and cause the duct gases to flow over the outer housing means and the inner chamber means;

said outer housing means and said inner chamber means being configured and dimensioned such that the Reynolds number for said flow of duct gases over the outer housing means and the inner chamber means is sub-critical but greater than that for laminar flow when said outer housing means is in said other position; and means for moving said outer housing means between said one position and said other position.

2. The sample chamber of claim 1 wherein said outer housing means has a configuration generally of a hollow, apertured cylinder.

3. The sample chamber of claim 1 wherein said cylinder comprises a right circular cylinder.

4. The sample chamber of claim 2 wherein said outer housing apertures are substantially diametrically opposed to one another across the axis of said cylinder.

5. The sample chamber of claim 2 wherein said inner chamber means has a generally cylindrical configuration with its cylindrical axis generally coincident with said outer housing cylindrical axis.

6. The sample chamber of claim 4 wherein said outer housing means and said inner chamber means comprise concentric right circular cylindrical means, and wherein said movement of said outer housing means between said one position and said other position comprises rotational movement about said outer housing axis.

7. The sample chamber of claim 5 wherein said outer housing apertures are substantially diametrically opposed to one another and said inner chamber apertures are substantially diametrically opposed to one another.

8. The sample chamber of claim 6 wherein each said aperture subtends an arc of less than 90°.

9. The sample chamber of claim 5 wherein the radially outer surface of said cylindrical inner chamber means is spaced from the radially inner surface of said outer housing means, whereby gases may flow between said spaced surfaces.

10. The sample chamber of claim 1 further comprising a source of pressurized air connected to the interior of said inner chamber means for supplying air thereto.

11. The sample chamber of claim 1 wherein said inner chamber means is elongated and extends longitudinally generally parallel to outer housing means axis, and wherein said inner chamber means further includes window means extending at least partially across one longitudinal end thereof, said window means being releasably mounted to said inner chamber means.

12. In a duct having a gas of predetermined density and viscosity flowing therethrough at a predetermined velocity a sample chamber for a gas analyzer for use in such duct, comprising outer housing means having the configuration generally of a hollow cylinder having an axis extending longitudinally thereof with at least a pair of longitudinally extending apertures on opposite sides of a plane which includes said axis, said outer housing means extending into said duct from one side of said duct with said axis generally transverse to the flow of gases within said duct, said outer housing means being movable between one position in which said apertures are generally aligned with said flow of gases to facilitate the passage of said gases therethrough, and another position in which said apertures face generally transverse to said flow of gases;

inner chamber means extending within said outer housing means and having apertures positioned to be aligned with said outer housing apertures when said outer housing apertures are generally aligned with said flow of gases, whereby the duct gases may pass freely through the apertures and inner chamber when the outer housing is in the one position and the gases will be deflected to flow over the outer housing means and inner chamber means when the outer housing means is in its other position;

said outer housing means and said inner chamber means being configured and dimensioned such that the Reynolds number for said flow of gases over the outer housing means and inner chamber means is sub-critical but greater than that for laminar flow when said outer housing means is in said other position; and means for moving said outer housing means between said one position and said other position.

13. The sample chamber of claim 12 wherein said outer housing means and said inner chamber means comprise concentric right circular cylinder means and wherein the radially outer surface of said cylindrical inner chamber means is spaced from the radially inner surface of said outer housing means.

14. The sample chamber of claim 13 further comprising tab means projecting radially outwardly from said inner chamber means outer surface, said tab means being positioned upon said inner chamber means such that, when said outer housing means is in said other position with said outer housing apertures facing generally transverse to said flow of gases, said tab means are upstream from the downstream edge of each of said outer housing apertures, with respect to said flow of gases, whereby the tab means may serve to create turbulence in the gases flowing over the outer surface of the inner chamber means which is exposed through the outer housing apertures.

15. The sample chamber of claim 14 wherein said tab means extend longitudinally on said inner chamber means for substantially the entire longitudinal extent of said outer housing means apertures.

* * * * *